(12) United States Patent
Wan

(10) Patent No.: US 9,918,862 B2
(45) Date of Patent: Mar. 20, 2018

(54) INTERNAL COVERING MEMBRANE OF DUODENUM

(71) Applicant: Ping Wan, Shanghai (CN)

(72) Inventor: Ping Wan, Shanghai (CN)

( * ) Notice: Subject to any disclaimer, the term of this patent is extended or adjusted under 35 U.S.C. 154(b) by 168 days.

(21) Appl. No.: 14/781,479

(22) PCT Filed: Mar. 28, 2014

(86) PCT No.: PCT/CN2014/074332
§ 371 (c)(1),
(2) Date: Sep. 30, 2015

(87) PCT Pub. No.: WO2014/161446
PCT Pub. Date: Oct. 9, 2014

(65) Prior Publication Data
US 2016/0030221 A1   Feb. 4, 2016

(30) Foreign Application Priority Data

Mar. 31, 2013   (CN) .......................... 2013 1 0107770

(51) Int. Cl.
*A61F 5/00* (2006.01)
*A61F 2/04* (2013.01)

(52) U.S. Cl.
CPC .............. *A61F 5/0076* (2013.01); *A61F 2/04* (2013.01); *A61F 2002/045* (2013.01); *A61F 2210/0004* (2013.01); *A61F 2220/0016* (2013.01)

(58) Field of Classification Search
CPC .................. A61F 5/0076; A61F 5/0089; A61F 2002/045; A61F 2210/0004; A61F 2220/0016; A61F 2/04
See application file for complete search history.

(56) References Cited

U.S. PATENT DOCUMENTS

| 8,834,553 | B2 * | 9/2014 | Melanson | A61F 2/04 |
| | | | | 606/151 |
| 2005/0125020 | A1 * | 6/2005 | Meade | A61B 17/0401 |
| | | | | 606/191 |
| 2009/0182355 | A1 * | 7/2009 | Levine | A61F 5/0076 |
| | | | | 606/153 |

FOREIGN PATENT DOCUMENTS

| CN | 102166142 A | 8/2011 |
| CN | 201987704 U | 9/2011 |

(Continued)

OTHER PUBLICATIONS

Zhixue Liu, "Healing Efficacy Evaluation Standards of Surgical Treatment of Diabetes Need to be Established—Interview with Peter Maomin Song, who is Vice President and Secretary of Party Committee of Beijing Tiantan Hospital Affiliated to Capital Medical University," *China Medical Herald*, vol. 8, No. 32, pp. 2-4 (Nov. 2011).

(Continued)

*Primary Examiner* — Leslie Deak
(74) *Attorney, Agent, or Firm* — Muncy, Geissler, Olds & Lowe, P.C.

(57) ABSTRACT

A duodenum internal covering membrane is disclosed. The covering membrane is made of a biocompatible material and mainly comprises an elastic ampulla and a tubular part, wherein the ampulla is positioned in the duodenal bulb, the tubular part can extend to the jejunum, the ampulla contains a wavy or V-shaped or trapezoidal or city wall-shaped elastic ring which is continuously encircled, the elastic ring is made of a memory or non-memory biocompatible material, peaks, valleys and bent angles of the elastic ring are single-circle coil springs with outward anchor hooks, the single-circle coil springs on the lower edge are penetrated and wound with recovery threads, the upper edge of the ampulla is a wavy or V-shaped or trapezoidal or city wall-shaped elastic (Continued)

membrane, the elastic ring and the ampulla comply with the motion of the duodenum and the bulb as a whole, and the ampulla and the tubular part can be closed up or folded into the shape of a ball or cylinder or capsule or spindle. The single-circle coil springs have strong elasticity, weak sharp injuries and good fixation for the recovery threads attached thereon, thereby being conductive to anatomical structure and basic physiological functions of the duodenum. The covering membrane within the duodenum of the present invention can be prepared into a medical device for preventing and treating obesity and diabetes.

4 Claims, 1 Drawing Sheet

(56) References Cited

FOREIGN PATENT DOCUMENTS

| CN | 101843536 B | 1/2012 |
|----|----|----|
| CN | 202113191 U | 1/2012 |
| CN | 102579104 A | 7/2012 |
| CN | 102626330 A | 8/2012 |
| CN | 103142262 A | 6/2013 |
| CN | 203169227 U | 9/2013 |
| WO | WO 2011/031981 A1 | 3/2011 |

OTHER PUBLICATIONS

Kao et al., "Research Progress of Surgical Treatment of Diabetes Mellitus," *J. Clin. Surg.*, vol. 17, No. 5, pp. 344-345 (May 2009).

Du et al., "Surgical Treatment of Diabetes Needs Regulation and Multidisciplinary Collaboration—Interveiw with Liyong Zhong, who is Endocrinology Professor of Beijing Tiantan Hospital Affiliated to Capital Medical University," *China Medicine and Pharmacy*, vol. 1, No. 22, pp. 1-2 (Nov. 2011).

Wen Lin, "A New Way of Treatment of Diabetes—Surgical Treatment," *China Medicine and Pharmacy*, vol. 1, No. 20, pp. 1-2 (Oct. 2011).

Yu et al., "Observation of the Curative Effect of Gastrojejunal Bypass Operation in the Treament of Diabetes Mellitus," *Jilin Medical Science*, vol. 32, No. 8, pp. 5912-5913 (Oct. 2011).

Anonymous, "Expert Interpretation: Weight Loss Surgery for Diabetes Treatment," *Diabetes World: Digest*, p. 51 (Oct. 2011).

Ji et al., "Surgical Treatment of Diabetes Expert Consensus," *Chinese J. of Diabetes*, vol. 3, No. 3, pp. 205-208 (Jun. 2011).

Yisheng Feng, "Gold Autumn Meeting, Multidisciplinary Experts' "Consultation" on Diabetes Surgery—Surgical Treatment of Diabetes Heaven 2011 Conference" Held in Beijing, *China Medicine and Pharmacy*, vol. 1, No. 21, pp. 3-5 (Nov. 2011).

Shi et al., "Development Prospect of Operation for the Treatment of Type 2 Diabetes Mellitus in China," *China Medical News*, vol. 26, No. 21, p. 1 (Nov. 2011).

* cited by examiner

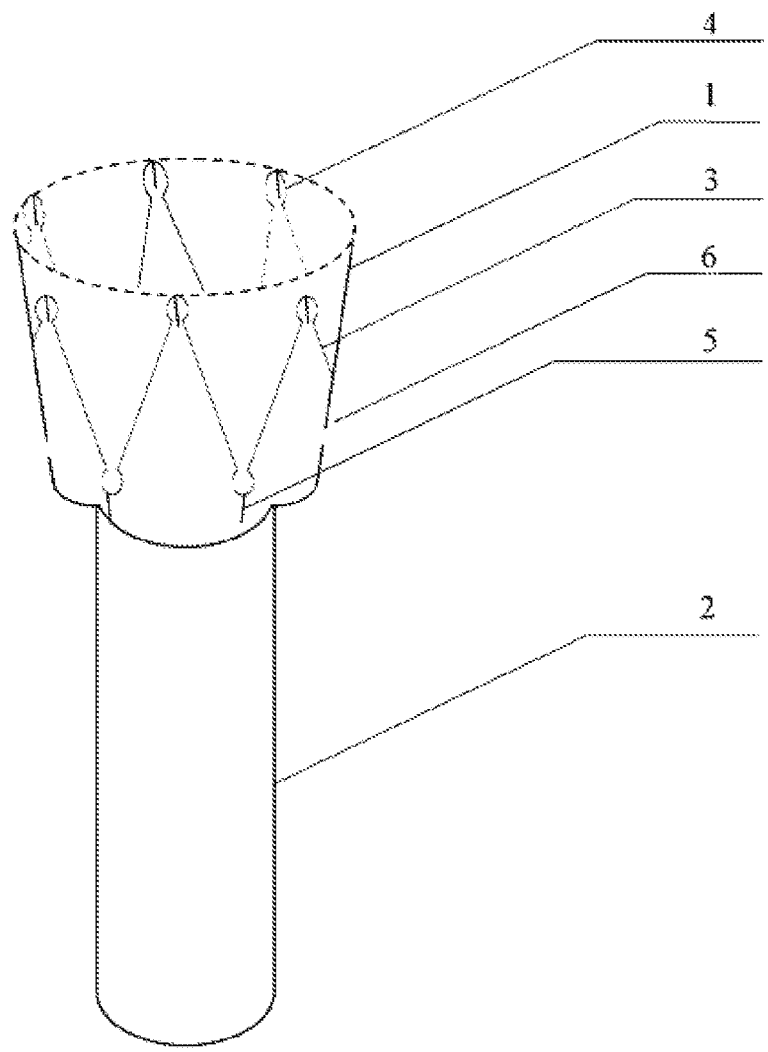

INTERNAL COVERING MEMBRANE OF DUODENUM

FIELD OF THE INVENTION

The present invention relates to a medical device placed in the digestive tract and, more particular, relates to a duodenum internal covering membrane for preventing and treating obesity and diabetes.

BACKGROUND OF THE INVENTION

Gastric bypass surgery can treat obesity. Recently, it was found that, for an obese patient undergoing the surgery, not only the body weight was significantly decreased, but also the type 2 diabetes complicated by obesity was alleviated (*Chinese Journal of Diabetes*, 2011, 3(3): 205-208): after the surgery, the blood sugar problem could be solved without injecting insulin or taking multiple medicaments, and hypertension, obesity, blood lipid disorders and other diabetic complications could be further obviously improved. According to the analysis of 22094 cases of the gastric bypass surgery: 84% of the patients suffering from the type 2 diabetes completely reversed after the surgery, and most of the patients stopped the treatment with oral medicaments or insulin before leaving the hospitals (*Chinese Medical Science*, 2011, 1 (21): 3-5). Foreign countries including the US government have been actively promoting the development of the surgery. In March, 2011, in the 2nd International Conference of Interventional Treatment of Type 2 Diabetes held in New York, US, the International Diabetes Federation (IDF) firstly issued a statement that, it was considered that the gastric bypass surgery can be used for treating the obese patients suffering from the type 2 diabetes and could reduce the occurrence and development of chronic complications of the diabetes (*Chinese Medical Science*, 2011, 1 (22): 1-2), and if the surgery was performed early, the serious complications of the diabetes could also be prevented (Diabetes World: Abstracts Journal, 2011, 10: 51).

However, the "gastric bypass surgery" has clinical risks, such as death, intestinal obstruction, anastomotic leakage, pulmonary embolism, deep vein thrombosis, portal vein injury, diseases of respiratory system and the like (*Chinese Journal of Diabetes*, 2011, 3 (3): 205-208). Thus, the way of placing the covering membrane within the duodenum in the duodenum in vivo for preventing and treating the obesity and the diabetes has an application significance for replacing the "gastric bypass surgery".

In the invention patent of "duodenal sleeve and conveyor thereof" (application date: Apr. 9, 2010 and date of authorized announcement: Jan. 11, 2012) in the prior art, although a disposable static "expanded" metal framework which covers an outer sleeve and only depends on "a memory alloy" is "fully close to" the intestinal wall and "the metal framework of a duodenal bulb cavity section" which is shaped like a "bowl and funnel" is "jointed with the duodenal bulb cavity", the duodenum is mobile, particularly when the gastric pylorus expands and draws the duodenal bulb which is just below the gastric pylorus to expand on the upper edge of the duodenal bulb, the metal framework is difficult to perform elastic expansion and accordingly move to the distal end of the duodenum, and when the gastric pylorus retracts, the metal framework may perform reverse reset (the mucosa of the duodenal bulb is relatively thin and is the predilection site of ulcers; and if the process is repeated in such a way, the mucosa is liable to injuries, and a muscular wall stretch receptor is liable to stimulation, thereby being liable to inducing nausea or/and vomiting [Zhou Lv, Ke Meiyun: *Gastrointestinal Dynamics*: Base and Clinic page 117] or perform incarceration at the distal end of the duodenal bulb by flexible intestinal compensative expansion. "The top end of the metal framework terminates on the side of the duodenal papilla near the pylorus", although it "does not hinder effluent of the bile and pancreatic duct from flowing out and entering the intestinal cavity", the back section of the metal framework duodenal bulb is "fully close to" the intestinal wall, and the duodenal papilla at a common opening of the common bile duct and the pancreatic duct at the lower end of the duodenal descending part is also blocked.

In order to solve the problem of fixation, according to the prior art (utility model patent of "sleeve placed in duodenum-jejunum" with the application date of Dec. 6, 2010 and date of authorized announcement of Sep. 28, 2011), a hollow metal tube is made into a spike fixing claw, which is "sleeved on metal wires of an annular stent" and is tightly "fixed". Then, in order to solve the removal problem in the future, according to the prior art (utility model patent of "sleeve placed in duodenum-jejunum"), a tightening thread is further designed, wherein the tightening thread is "placed at the top of the annular stent", and "can be wound around an upper opening for one circle or multiple circles", but by implanting the sleeve in vivo, particularly under the situation of only considering that the spike fixing claw made of the hollow metal tube on the static annular stent with "simplicity and convenience in manufacturing and tightening performance" is pierced into the inner wall of the duodenal bulb cavity, and along with the gastrointestinal motion, looseness, exudation and adhesion are repeated continuously. According to the prior art (utility model patent of "sleeve placed in duodenum-jejunum"), the material of a flexible tube only considers "smooth surface, softness and compactness", the adaptive elastic expansion and contraction of the annular stent to the movements of the duodenal bulb and the adoption of the elastic material for preparing the flexible tube are not involved in the patent; and the tightening thread without elasticity which is "fixed" at "the top of the annular stent" on the upper edge of the duodenal bulb even limits the compliance of the annular stent to the movements of the duodenal bulb. Compared with the invention patent of "duodenal sleeve and conveyor thereof" in the prior art, in the prior art (utility model patent of "sleeve placed in duodenum-jejunum"), as the annular stent and the spike fixing claw are only positioned in the duodenal bulb, although the duodenal papilla at the common opening of the common bile duct and the pancreatic duct at the lower end of the duodenal descending part is not blocked, but if they are placed on the upper edge of the duodenal bulb, when the gastric pylorus expands or retracts to draw the duodenal bulb which is just below the gastric pylorus to move (Zhou Lv, Ke Meiyun: *Gastrointestinal Dynamics: Base and Clinic* pages 381, 520 and 522), the annular stent and the spike fixing claw are bound to hinder the movements of the duodenal bulb, particularly when the gastric pylorus expands to draw the duodenal bulb to move, the annular stent and the spike fixing claw cannot accordingly expand, the spike fixing claw pierced into the mucosa of the duodenal bulb also inwards and centrically pulls the mucosal tissue of the duodenal bulb to be opposite to the movements of muscle tissue and other tissues below the mucosa of the duodenal bulb, which are expanded outwards and centrifugally as a whole, and obviously, when the gastric pylorus expands or retracts to draw the duodenal bulb which is just below the gastric pylorus to move, such annular stent and the spike fixing claw which cannot change or change a little accordingly can cause injuries to the duodenal bulb; and if they are placed on the lower edge of the duodenal bulb, although the drawing of the lower edge of the duodenal bulb by expansion or retraction of the gastric pylorus is less than the drawing of the upper edge of the duodenal bulb, even the injuries to the mucosa of the duodenal bulb caused by the annular stent and the spike fixing claw thereof are ignored, the original effect of blocking the duodenal bulb also disappears accordingly.

In the prior art (utility model patent of "sleeve placed in duodenum-jejunum" with application date of Dec. 6, 2010 and date of authorized announcement of Sep. 28, 2011), the metal wires of the annular stent are continuous like V, the elasticity of such model is weaker than that of the model which arranges single-circle coil springs in V-shaped peaks, valleys and bent angles and is prepared from the same material by the same preparation method, the sharp injuries of the model are stronger than that of the model which arranges the single-circle coil springs in the V-shaped peaks, the valleys and the bent angles and is prepared from the same material by the same preparation method, the fixation of "scissors open" against buckling threads or recovery threads attached thereon of such model is also poorer than that of the model which arranges the single-circle coil springs in the V-shaped peaks, the valleys and the bent angles and is prepared from the same material by the same preparation method, and the fixation against the buckling threads or the recovery threads in the intestinal cavity of the duodenum performing telescopic motion in the transverse diameter and conveying chyme in the longitudinal diameter is poorer, thereby being not conductive to anatomical structure and basic physiological functions.

SUMMARY OF THE INVENTION

The invention aims at solving the following technical problems:

In the invention patent of "duodenal sleeve and conveyor thereof" (application date: Apr. 9, 2010 and date of authorized announcement: Jan. 11, 2012) in the prior art, for a disposable static "expanded" and "bowl and funnel-shaped" "a metal framework of a duodenal bulb cavity section" which covers an outer sleeve and only depends on "a memory alloy", when the gastric pylorus expands and draws the duodenal bulb which is just below the gastric pylorus to expand, the metal framework is difficult to perform elastic expansion and accordingly move to the distal end of the duodenum, and when the gastric pylorus retracts, the metal framework may perform reverse reset (mucosa is liable to injuries) or perform incarceration at the distal end of the duodenal bulb by flexible intestinal compensative expansion. The upper section of a duodenum internal covering membrane of the present invention can be a wavy or V-shaped or trapezoidal or city wall-shaped ampulla elastic membrane, the ampulla elastic membrane contains a wavy or V-shaped or trapezoidal or city wall-shaped elastic ring which is continuously encircled, the elastic ring can be made of a memory or non-memory biocompatible material, peaks, valleys and bent angles of the elastic ring can be single-circle coil springs with outward anchor hooks, and the covering membrane can perform telescopic or elastic movements by complying with the motion of the duodenum and the bulb as a whole, thereby solving this problem.

In the invention patent of "duodenal sleeve and conveyor thereof" (application date: Apr. 9, 2010 and date of authorized announcement: Jan. 11, 2012) in the prior art, the back section of the metal framework duodenal bulb blocks the duodenal papilla at a common opening of the bile duct and the pancreatic duct at the lower end of the duodenal descending part. In the present invention, the elastic ring is just positioned in the duodenal bulb and does not block the duodenal papilla at the common opening of the bile duct and the pancreatic duct at the lower end of the duodenal descending part, thereby solving this problem.

In order to solve the problem of fixation, according to the utility model patent of "sleeve placed in duodenum-jejunum" in the prior art (with application date of Dec. 6, 2010 and date of authorized announcement of Sep. 28, 2011), a spike fixing claw which is made of a hollow metal tube on a static annular stent which only considers "simplicity and convenience in manufacturing and tightening performance") is pierced into the inner wall of the duodenal bulb cavity. According to the prior art (utility model patent of "sleeve placed in duodenum-jejunum"), the material of a flexible tube only considers "smooth surface, softness and compactness", the adaptive elastic expansion and contraction of the annular stent to the movements of the duodenal bulb and the adoption of the elastic material for preparing the flexible tube are not involved in the patent; and the tightening thread without elasticity which is "fixed" at "the top of the annular stent" on the upper edge of the duodenal bulb even limits the compliance of the annular stent to the movements of the duodenal bulb. If the annular stent and the spike fixing claw are placed on the upper edge of the duodenal bulb, when the gastric pylorus expands or retracts to draw the duodenal bulb which is just below the gastric pylorus to move, the annular stent and the spike fixing claw are bound to hinder the movements of the duodenal bulb, particularly when the gastric pylorus expands to draw the duodenal bulb to move, the annular stent and the spike fixing claw cannot accordingly expand, the spike fixing claw pierced into the mucosa of the duodenal bulb also inwards and centrically pulls the mucosal tissue of the duodenal bulb to be opposite to the movements of muscle tissue and other tissues below the mucosa of the duodenal bulb, which are expanded outwards and centrifugally as a whole, and obviously, when the gastric pylorus expands or retracts to draw the duodenal bulb which is just below the gastric pylorus to move, such annular stent and the spike fixing claw which cannot change or change a little accordingly can cause injuries to the duodenal bulb; and if the annular stent and the spike fixing claw are placed on the lower edge of the duodenal bulb, although the drawing of the lower edge of the duodenal bulb by the expansion or retraction of the gastric pylorus is less than the drawing of the upper edge of the duodenal bulb, even the injuries to the mucosa of the duodenal bulb caused by the annular stent and the spike fixing claw thereof are ignored, the original effect of blocking the duodenal bulb also disappears accordingly. The ampulla elastic membrane and the elastic ring contained therein of the invention can perform telescopic or elastic motion by complying with the motion of the duodenum and the bulb as a whole, thereby not only reducing the injuries to the mucosa of the duodenal bulb, but also blocking the duodenal bulb. Thus, this problem can be solved. Secondly, recovery threads penetrating and winding single-circle coil springs on the lower edge of the elastic ring are positioned on the lower edge of the duodenal bulb with relatively small relative extension and do not affect the compliance to the motion of the duodenum and the bulb, and when the internal covering membrane is recovered, the recovery threads are pulled to the upper end and pulled into the single-circle coil springs on the upper edge of the elastic ring via a duct of endoscopic pliers, then the anchor hooks can be pulled out and the elastic rings can be folded up to recover the covering membrane within the duodenum of the present invention.

In the prior art (utility model patent of "sleeve placed in duodenum-jejunum" with application date of Dec. 6, 2010 and date of authorized announcement of Sep. 28, 2011), the metal wires of the annular stent are continuous like V, and compared with the model which arranges the single-circle coil springs in V-shaped peaks, valleys and bent angles and is prepared from the same material by the same preparation method, such model has weaker elasticity, stronger sharp injuries and poorer fixation against buckling threads or the recovery threads attached thereon. The elastic ring of the present invention can also be continuous like V. But the single-circle coil springs are arranged in the V-shaped peaks, the valleys and the bent angles of the elastic ring, and such single-circle coil springs have stronger elasticity, weaker sharp injuries and better fixation against the buckling threads or the recovery threads attached thereon in comparison with the prior art (utility model patent of "sleeve placed in duodenum-jejunum" with application date of Dec. 6, 2010 and date of authorized announcement of Sep. 28, 2011), thereby being conductive to anatomical structure and basic physiological functions of the duodenum.

The technical solution adopted by the invention is as follows:

All the parts of the duodenum internal covering membrane can be made of biocompatible biodegradable or non-biodegradable materials.

The covering membrane within the duodenum can be divided into an ampulla and a tubular part, wherein the ampulla is positioned in the duodenal bulb and the tubular part can extend to the jejunum.

The diameter, the length and the thickness of the tubular part can be matched with the duodenum and the jejunum in each person of different people groups. Preferably, the diameter is 10-60 mm, the length is matched with the duodenum and can extend to one section of the jejunum following the duodenum, the length is 80-700 mm, and the thickness of the internal covering membrane of the tubular part is 0.005 mm-1 mm.

The ampulla is a flared part following the tubular part. Preferably, the ampulla can be cylindrical, spherical and waist drum-shaped. Preferably, the thickness of the internal covering membrane of the ampulla is 0.005 mm-1 mm, the height is 6 mm-100 mm, and the flared part following the tubular part forms a progressive open acute angle, which is preferably 5° C.-65° C. The thickness, the height and the angle can be matched with different people groups.

Preferably, the upper edge of the ampulla of the covering membrane within the duodenum can be a wavy or V-shaped or trapezoidal or city wall-shaped elastic membrane, and the ampulla contains a wavy or V-shaped or trapezoidal or city wall-shaped elastic ring which is continuously encircled. Preferably, the wire diameter of the elastic ring can be 0.05 mm-1 mm, the diameter of single-circle coil springs in peaks, valleys and bent angles can be 0.5 mm-5 mm, and the elastic ring and the ampulla can be combined into a whole. Preferably, the flattened elastic ring can be wavy or V-shaped or trapezoidal or city wall-shaped elastic ring with single-circle coil springs in the peaks, the valleys and the bent angles. The flattened elastic ring in various shapes can encircle the ampulla in single circle or multiple circles. Preferably, the included angle between anchor hooks is 5° C.-75° C. Preferably, the length of the anchor hooks is 0.3 mm-10 mm.

Preferably, the elastic ring of the ampulla of the covering membrane within the duodenum can be made of a memory or non-memory biocompatible material, and the elastic ring and the ampulla can perform telescopic or elastic movements by complying with the motion of the duodenum and the bulb as a whole.

Preferably, recovery threads penetrating and winding the single-circle coil springs on the lower edges of the peaks, the valleys and the bent angles of the elastic ring can select biocompatible corrosion-resistant memory or non-memory high polymer materials and metals. When the covering membrane within the duodenum is recovered, the recovery threads are pulled to the upper end and pulled into the single-circle coil springs on the upper edge of the elastic ring via a duct of endoscopic pliers, then the anchor hooks can be pulled out and the elastic rings can be folded up to recover the covering membrane within the duodenum of the present invention.

Preferably, the ampulla and the tubular part of the covering membrane within the duodenum can be closed up or folded into the shape of a ball or cylinder or capsule or spindle in vitro.

The covering membrane within the duodenum is soft, smooth, elastic and good in tissue compatibility, and has no acute systemic reaction, no chronic systemic reaction, no acute local reaction and no chronic local reaction.

The covering membrane within the duodenum can be sent into the duodenum via the upper digestive tract under the assistance of an endoscope and X-ray fluoroscopy, if the memory material is adopted, the covering membrane can be gradually spread out, the ampulla of the internal covering membrane is placed at the upper part of the duodenum, and the lower edge of the ampulla is arranged on the side of the duodenal papilla and the minor papilla near the gastric pylorus and does not hinder liquid from the bile duct and the pancreatic duct from entering the intestinal cavity. The tubular part of the internal covering membrane is positioned at the duodenal descending part, the horizontal part and the ascending part following the upper part of the duodenum and the extended tubular part is positioned in the jejunum section following the ascending part of the duodenum.

The anchor hooks encircled on the elastic ring of the ampulla of the covering membrane within the duodenum are inserted into the mucosa and the submucosal tissue of the duodenum bulb cavity section correspondingly, thereby fixing the covering membrane within the duodenum in the duodenum.

The covering membrane within the duodenum diverts chyme and bile and pancreatic juice in vivo, avoids direct digestion, absorption and metabolism of gastric effluent in the duodenum, and can be prepared into a medical device for preventing and treating obesity and diabetes.

The recovery threads penetrating and winding single-circle coil springs on the lower edge of the elastic ring are positioned on the lower edge of the duodenal bulb with relatively small relative extension and do not affect the compliance to the motion of the duodenum and the bulb, and when the internal covering membrane is recovered, the recovery threads are pulled to the upper end and pulled into the single-circle coil springs on the upper edge of the elastic ring via a duct of endoscopic pliers, then the anchor hooks can be pulled out and the elastic rings can be folded up to recover the covering membrane within the duodenum of the present invention.

The length and the thickness of each part, the number of circles of the elastic ring, the diameter of the small rings in the peaks, the valleys and the bent angles and the number of circles of the covering membrane within the duodenum are reference values, and can be specifically designed according to needs in actual manufacturing.

The invention has the following beneficial effects:

The present invention provides a duodenum internal covering membrane, characterized in that the covering membrane is made of a biocompatible biodegradable or non-biodegradable material and mainly comprises an elastic ampulla and a tubular part, wherein the ampulla is positioned in the duodenal bulb, the tubular part can extend to the jejunum, the ampulla contains a wavy or V-shaped or trapezoidal or city wall-shaped elastic ring which is continuously encircled, the elastic ring can be made of a memory or non-memory biocompatible material, peaks, valleys and bent angles of the elastic ring can be single-circle coil springs with outward anchor hooks, the single-circle coil springs on the lower edge are penetrated and wound with recovery threads, the upper edge of the ampulla can be a wavy or V-shaped or trapezoidal or city wall-shaped elastic membrane, the elastic ring and the ampulla can perform telescopic or elastic movements by complying with the motion of the duodenum and the bulb as a whole, and the ampulla and the tubular part can be closed up or folded into the shape of a ball or cylinder or capsule or spindle in vitro. By placing the internal covering membrane in the duodenum, the covering membrane can divert chyme and bile and pancreatic juice in vivo, avoid direct digestion, absorption and metabolism of gastric effluent in the duodenum, and can be prepared into a medical device for preventing and treating obesity and diabetes. Compared with the invention patent of "duodenal sleeve and conveyor thereof" (application date: Apr. 9, 2010 and date of authorized announcement: Jan. 11, 2012) in the prior art, the covering membrane within the duodenum of the invention can perform telescopic or elastic motion by complying with the motion of the duodenum and the bulb as a whole, thereby reducing the injuries to the duodenal bulb and avoiding the incarceration in the flexible intestinal duct; and the elastic ring of the ampulla of the covering membrane within the duodenum of the present invention does not block an opening of the bile duct and the pancreatic duct of the duodenum and does not hinder the effluent of the bile duct and the pancreatic duct from entering the intestinal tube. Compared with the utility model patent of "sleeve placed in duodenum-jejunum" (application date of Dec. 6, 2010 and date of authorized announcement of Sep. 28, 2011) in the prior art, the elastic membrane of the ampulla of the present invention and the elastic ring contained therein can perform telescopic or elastic motion by complying with the motion of the duodenum and the bulb as a whole, thereby not only reducing the injuries to the mucosa of the duodenal bulb, but also blocking the duodenal bulb. Compared with the utility model patent of "sleeve placed in duodenum-jejunum" (application date of Dec. 6, 2010 and date of authorized announcement of Sep. 28, 2011) in the prior art, the recovery threads penetrating and winding the single-circle coil springs on the lower edge of the elastic ring are positioned on the lower edge of the duodenal bulb with relatively small relative extension and do not affect the compliance to the motion of the duodenum and the bulb, and when the internal covering membrane is recovered, the recovery threads are pulled to the upper end and pulled into the single-circle coil springs on the upper edge of the elastic ring via a duct of endoscopic pliers, then the anchor hooks can be pulled out and the elastic rings can be folded up to recover the covering membrane within the duodenum of the present invention. Compared with the utility model patent of "sleeve placed in duodenum-jejunum" (application date of Dec. 6, 2010 and date of authorized announcement of Sep. 28, 2011) in the prior art, the single-circle coil springs arranged in the V-shaped peaks, the valleys and the bent angles of the elastic ring of the present invention have stronger elasticity, weaker sharp injuries and better fixation against buckling threads or the recovery threads attached thereon in comparison with the model prepared from the same material by the same preparation method, thereby being conductive to anatomical structure and basic physiological functions of the duodenum.

BRIEF DESCRIPTION OF THE DRAWINGS

The sole FIGURE is a schematic diagram of the structure.
In the sole FIGURE, the parts or the sites represented by the reference numbers are as follows: 1—ampulla; 2—tubular part; 3—elastic ring; 4—single—circle coil spring; 5—anchor hook; and 6—recovery thread.

DETAILED DESCRIPTION OF THE EMBODIMENTS

The present invention is further described below in conjunction with the accompanying drawing and the specific embodiments.

As shown in the drawing, the present invention provides a duodenum internal covering membrane. All the parts of the covering membrane within the duodenum can be made of biocompatible biodegradable or non-biodegradable materials. The covering membrane within the duodenum can be divided into an ampulla 1 and a tubular part 2, wherein the ampulla is positioned in the duodenal bulb and the tubular part can extend to the jejunum.

The diameter, the length and the thickness of the tubular part can be matched with the duodenum and the jejunum in each person of different people groups. Preferably, the diameter is 10-60 mm, the length is matched with the duodenum and can extend to one section of the jejunum following the duodenum, the length is 80-700 mm, and the thickness of the internal covering membrane of the tubular part is 0.005 mm-1 mm. The ampulla is a flared part following the tubular part. Preferably, the ampulla can be cylindrical, spherical and waist drum-shaped. Preferably, the thickness of the internal covering membrane of the ampulla is 0.005 mm-1 mm, the height is 6 mm-100 mm, and the flared part following the tubular part forms a progressive open acute angle, which is preferably 5° C.-65° C. The thickness, the height and the angle can be matched with different people groups.

Preferably, the upper edge of the ampulla of the covering membrane within the duodenum can be a wavy or V-shaped or trapezoidal or city wall-shaped elastic membrane, and the ampulla contains a wavy or V-shaped or trapezoidal or city wall-shaped elastic ring 3 which is continuously encircled. Preferably, the wire diameter of the elastic ring 3 can be 0.05 mm-1 mm, the diameter of single-circle coil springs 4 in peaks, valleys and bent angles can be 0.5 mm-5 mm, and the elastic ring 4 and the ampulla 1 can be combined into a whole. Preferably, the flattened elastic ring 3 can be wavy or V-shaped or trapezoidal or city wall-shaped elastic ring with single-circle coil springs 4 in the peaks, the valleys and the bent angles. The flattened elastic ring 3 in various shapes can encircle the ampulla 1 in single circle or multiple circles. Anchor hooks 5 are arranged on the single-circle coil springs 4 of the elastic ring 3, and the anchor hooks 5 face the end of the tubular part. Preferably, the included angle between the anchor hooks 5 is 5° C.-75° C. Preferably, the length of the anchor hooks 5 is 0.3 mm-10 mm.

Preferably, the elastic ring 3 of the ampulla of the covering membrane within the duodenum can be made of a memory or non-memory biocompatible material, and the elastic ring 3 and the ampulla 1 can perform telescopic or elastic movements by complying with the motion of the duodenum and the bulb as a whole. The peaks, the valleys and the bent angles of the elastic ring 3 can be the single-circle coil springs 4 with the outward anchor hooks, and the single-circle coil springs 4 on the lower edge are penetrated and wound with recovery threads 6.

Preferably, the recovery threads can select biocompatible corrosion-resistant memory or non-memory high polymer materials and metals.

Preferably, the ampulla and the tubular part of the covering membrane within the duodenum can be closed up or folded into the shape of a ball or cylinder or capsule or spindle in vitro. The covering membrane within the duodenum is soft, smooth, elastic and good in tissue compatibility, and has no acute systemic reaction, no chronic systemic reaction, no acute local reaction and no chronic local reaction.

The covering membrane within the duodenum can be sent into the duodenum via the upper digestive tract under the assistance of an endoscope and X-ray fluoroscopy, if the memory material is adopted, the covering membrane can be gradually spread out, the ampulla of the internal covering membrane is placed at the upper part of the duodenum, and the lower edge of the ampulla is arranged on the side of the duodenal papilla and the minor papilla (or micro papilla) near the gastric pylorus and does not hinder liquid from the bile duct and the pancreatic duct from entering the intestinal cavity. The tubular part of the internal covering membrane is positioned at the duodenal descending part, the horizontal part and the ascending part following the upper part of the duodenum and the extended tubular part is positioned in the jejunum section following the ascending part of the duodenum.

The anchor hooks encircled on the elastic ring of the ampulla of the covering membrane within the duodenum are inserted into the mucosa and the submucosal tissue of the duodenum bulb cavity section correspondingly, thereby fixing the covering membrane within the duodenum in the duodenum.

The covering membrane within the duodenum diverts chyme and bile and pancreatic juice in vivo, avoids direct digestion, absorption and metabolism of gastric effluent in the duodenum, and can be prepared into a medical device for preventing and treating obesity and diabetes.

The length and thickness of each part, the number of circles of the elastic ring, and the diameter of the single-circle coil springs in the peaks, the valleys and the bent angles of the covering membrane within the duodenum are reference values, and can be specifically designed according to needs in actual manufacturing.

Embodiment 1

A duodenum internal covering membrane can be made of a biocompatible biodegradable or non-biodegradable material and mainly comprises a tubular part 2 and a flared following ampulla 1, wherein an elastic ring 3 with anchor hooks 5 is encircled on the outer side of the ampulla 1.

The internal covering membrane at the ampulla 1 and the tubular part 2 can be prepared by an electrostatic spinning method. The thickness of the internal covering membrane at the ampulla 1 and the tubular part 2 is 0.01 mm, the diameter and the length of the tubular part 2 can be matched with the duodenum and the jejunum in each person of different people groups, the diameter is 25 mm, the tubular part 2 can extend to one section of the jejunum following the duodenum, and the length is 400 mm. The height of the flared following ampulla 1 is 25 mm, the flared following tubular part 2 forms a progressive open acute angle, and the angle is 45° C.

The single-circle elastic ring 3 is encircled on the outer side of the ampulla 1, the elastic ring 3 and the ampulla 1 are combined into a whole, the wire diameter of the elastic ring 3 is 0.05 mm, the flattened elastic ring 3 is V-shaped, each single-circle coil spring 4 of the elastic ring 3 is attached with an anchor hook, the length of the anchor hooks 5 is 1 mm, the anchor hooks 5 face the end of the tubular part, and the included angle 4 is 45° C. The integral elastic ring 3 can be electrospun when the internal covering membrane at the ampulla 1 and the tubular part 2 is prepared by the electrostatic spinning method, and can be glued after the internal covering membrane at the ampulla 1 and the tubular part 2 are prepared and formed by the electrostatic spinning method.

After the preparation of the internal covering membrane at the ampulla 1 and the tubular part 2, attached with the integral elastic ring 3, the single-circle coil springs 4 on the lower edge of the elastic ring 3 are manually penetrated and wound with recovery threads 6 in the consistent penetration and winding direction, the lamination is performed around the lower edge of the ampulla 3 by one circle, the surplus length is cut off, and the head and tail ends are knotted or the head and tail ends are laminated.

The covering membrane within the duodenum of the patent after preparation is regularly folded into the ampulla 3, the elastic ring 3 of the ampulla 1 is centrically folded up, then the covering membrane within the duodenum of the patent is shaped like a spindle or an olive, and then the covering membrane is placed into a pusher and precisely placed into the duodenal bulb and the extension section thereof by an endoscope and X-ray fluoroscopy.

When the covering membrane within the duodenum of the patent is recovered, the recovery threads 6 are pulled to the upper end and pulled into the single-circle coil springs 4 on the upper edge of the elastic ring 3 via a duct of endoscopic pliers, then the anchor hooks 5 can be pulled out and the elastic rings 3 can be folded up to recover the covering membrane within the duodenum of the present invention.

The length, the thickness, the diameter and the like of each part of the present invention are reference values and can be specifically designed according to individual needs in actual manufacturing.

The parts to which the present invention does not relate contain the same contents as the prior art or can be implemented by adopting the prior art.

What is claimed is:
1. A duodenum internal covering membrane, comprising:
   a covering membrane made of a biocompatible material, the covering membrane comprising:
   an elastic ampulla and a tubular part,
   wherein the ampulla is positioned in a duodenal bulb and the tubular part extends to a jejunum,
   wherein the ampulla contains an elastic ring having a continuous wall,
   wherein the continuous wall comprises an upper edge and a lower edge, with the lower edge being positioned closest to the tubular part, the upper edge of the continuous wall being wavy or V-shaped or trapezoidal or crenellated, wherein peaks, valleys, and bent angles of the upper edge comprise anchor hooks which are connected to the wall via coil springs, wherein the coil springs on the lower edge are penetrated and wound with recovery threads, wherein the elastic ring and the ampulla perform telescopic or elastic movements by complying with the motion of the duodenum and the bulb as a whole, and wherein the ampulla and the tubular part are capable of being closed up or folded into a shape of a ball or cylinder or capsule or spindle in vitro.

2. The membrane of claim 1, wherein the covering membrane is made of biodegradable material.

3. The membrane of claim 2, wherein the elastic ring is made of a memory material.

4. The membrane of claim 1, wherein the elastic ring is made of a memory material.

\* \* \* \* \*